(12) United States Patent
Cleary et al.

(10) Patent No.: US 6,913,460 B2
(45) Date of Patent: Jul. 5, 2005

(54) COUPLING FOR ORTHODONTIC ASSEMBLY

(75) Inventors: James D. Cleary, Glendora, CA (US); John J. Palmer, Monrovia, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 190 days.

(21) Appl. No.: 10/171,353

(22) Filed: Jun. 12, 2002

(65) Prior Publication Data

US 2003/0232301 A1 Dec. 18, 2003

(51) Int. Cl.$^7$ .................................................. A61C 3/00
(52) U.S. Cl. .......................................... 433/19; 433/17
(58) Field of Search ................................ 433/5, 17, 18, 433/19, 21, 22, 24

(56) References Cited

U.S. PATENT DOCUMENTS

| | | | |
|---|---|---|---|
| 3,798,773 A | | 3/1974 | Northcutt |
| 3,903,604 A | * | 9/1975 | Snead .............................. 433/5 |
| 4,038,754 A | * | 8/1977 | Armstrong ...................... 433/5 |
| 4,087,915 A | * | 5/1978 | Andrews ......................... 433/5 |
| 4,212,637 A | * | 7/1980 | Dougherty et al. ............ 433/5 |
| 4,226,589 A | | 10/1980 | Klein |
| 4,245,984 A | * | 1/1981 | Hamill, Jr. ..................... 433/5 |
| 4,368,039 A | | 1/1983 | Armstrong |
| 4,392,826 A | * | 7/1983 | Goshgarian .................... 433/7 |
| 4,406,620 A | | 9/1983 | Kaprelian et al. |
| 4,462,800 A | | 7/1984 | Jones |
| 4,551,095 A | | 11/1985 | Mason |
| 4,553,934 A | | 11/1985 | Armstrong et al. |
| 4,588,380 A | * | 5/1986 | Toll ............................... 433/5 |
| 4,708,646 A | | 11/1987 | Jasper |
| 4,815,972 A | * | 3/1989 | Howe ............................. 433/5 |
| 5,352,116 A | | 10/1994 | West |
| 5,435,721 A | | 7/1995 | Vogt |
| 5,562,445 A | | 10/1996 | DeVincenzo et al. |
| 5,645,423 A | | 7/1997 | Collins, Jr. |
| 5,645,424 A | | 7/1997 | Collins, Jr. |
| 5,651,672 A | | 7/1997 | Cleary et al. |
| 5,678,990 A | | 10/1997 | Rosenberg |
| 5,695,332 A | * | 12/1997 | Samuels ......................... 433/5 |
| 5,711,667 A | | 1/1998 | Vogt |
| 5,846,074 A | | 12/1998 | Klapper |
| 5,964,588 A | | 10/1999 | Cleary |
| 5,980,247 A | | 11/1999 | Cleary |
| 6,053,730 A | | 4/2000 | Cleary |
| 6,113,390 A | * | 9/2000 | Sirney et al. ................. 433/19 |
| 6,120,289 A | | 9/2000 | Cleary et al. |
| 6,183,250 B1 | * | 2/2001 | Kanno et al. ................. 433/17 |
| 6,217,323 B1 | * | 4/2001 | Liou ............................. 433/18 |
| 6,234,791 B1 | | 5/2001 | Cleary et al. |
| 6,325,622 B1 | | 12/2001 | Kelly et al. |

OTHER PUBLICATIONS

U.S. Appl. No. 09/687,392; "Coupling For Orthodontic Applicance".

* cited by examiner

*Primary Examiner*—Ralph A. Lewis
(74) *Attorney, Agent, or Firm*—James D. Christoff (57) ABSTRACT

An orthodontic coupling includes a first portion and a second portion that are resiliently interconnected for movement toward and away from each other. The second portion is adapted for insertion into a passage of an orthodontic appliance, and the resilient connection between the first portion and the second portion releasably secures the coupling in place. The coupling is particularly useful for connecting force modules such as Class II correctors to buccal tube appliances.

26 Claims, 5 Drawing Sheets

COUPLING FOR ORTHODONTIC ASSEMBLY

BACKGROUND OF THE INVENTION

1. Field of the Invention

This invention relates to a coupling used in orthodontic treatment. The coupling is useful for connecting force modules or other devices to other orthodontic components in the oral cavity.

2. Description of the Related Art

Orthodontic therapy is a specialized form of treatment within the field of dentistry. Orthodontic treatment involves movement of malpositioned teeth to orthodontically correct locations. Orthodontic treatment often greatly improves the aesthetic appearance of the patient's teeth and also improves the patient's occlusion, so that when the jaws are closed the upper teeth are in proper positions relative to the lower teeth.

Orthodontic therapy is often carried out by use of a system of tiny appliances, wires and other components that are commonly known collectively as "braces". Typically, a small appliance known as a bracket is connected to each of the patient's anterior, cuspid and bicuspid teeth and an archwire placed in a slot of each bracket. The archwire forms a track to guide movement of the brackets and the associated teeth to desired positions.

End sections of orthodontic archwires are often held by appliances known as buccal tubes that are secured to the patient's molar teeth. Each buccal tube has a passage that slidingly receives the end section of the archwire. Buccal tubes may be placed on the patient's first molar teeth or the patient's second molar teeth.

In some instances, and particularly in connection with adolescent patients, the second molar tooth has often not sufficiently erupted at the beginning of orthodontic treatment to receive a buccal tube. In those instances, the practitioner may elect to install a convertible buccal tube on the patient's first molar teeth. Later, and after the second molar teeth have erupted, a buccal tube is installed on the second molar teeth and the buccal tube on the first molar teeth is converted to a bracket. Convertible buccal tubes have an enclosed passage that can be opened when desired to convert the passage into a slot that is open along one side, similar to the slots of orthodontic brackets.

In orthodontic treatment, the molar teeth often serve as convenient points of anchorage for various components because the molar teeth are relatively large and have a plurality of roots. As a consequence, many buccal tube appliances have a passage in addition to the passage for receiving the archwire slot. The additional passage (also known as an auxiliary passage) can be used for connection to other orthodontic devices as desired.

For example, the orthodontic treatment of some patients includes correction of the alignment of the upper dental arch to the lower dental arch. Certain patients have a condition referred to as a Class II malocclusion wherein the lower dental arch is located an excessive distance rearward of the upper dental arch when the jaws are closed. Other patients may have an opposite condition referred to as a Class III malocclusion wherein the lower dental arch is located forward of the upper dental arch when the jaws are closed.

In the past, correction of Class II and Class III malocclusions was often carried out by the use of a force-applying system known as headgear. The headgear includes strapping that extends around the rear of the patient's head, and the strapping is connected to a facebow having legs that are received in the passages of buccal tubes. An example of headgear is described in U.S. Pat. No. 4,368,039 to Armstrong. Optionally, each side of the strapping is connected to the facebow by a releasable coupling having a tension spring. The strapping and springs serve to apply a rearwardly-directed force to the buccal tube appliances and hence to the patient's associated jaw.

Intra-oral devices for correction of Class II and Class III malocclusions are also known. Such intra-oral devices are preferred by many patients who might otherwise be embarrassed by the appearance of headgear. Practitioners also often prefer intra-oral devices for correction of Class II and Class III malocclusions because, unlike headgear, many of those devices are fixed in place and issues of patient cooperation are avoided.

A number of intra-oral devices for correcting Class II and Class III malocclusions are known in the art. For example, U.S. Pat. Nos. 4,708,646, 5,352,116, 5,435,721 and 5,651,672 describe intra-oral devices with flexible spring members that are connected to upper and lower arches of a patient. The length of the device is selected such that the member is curved in an arc when the patient's jaws are closed. The inherent spring bias tends to urge the members toward a normally straight orientation and provide a force that pushes one dental arch forward or rearward relative to the other dental arch when the jaws are closed.

U.S. Pat. Nos. 5,645,424 and 5,678,990 describe intra-oral devices for correcting Class II and Class III malocclusions having linkage that includes pivotal connections. The devices in both of these references have an overall somewhat "Z"-shaped configuration. A device having a somewhat similar overall configuration is shown in U.S. Pat. No. 5,645,423 and includes double helical loops located on each side of a central segment. In U.S. Pat. No. 5,678,990, one of the linkages comprises a spring-loaded telescoping assembly.

Other orthodontic devices for correcting Class II and Class III malocclusions are described in U.S. Pat. Nos. 3,798,773, 4,462,800 and 4,551,095. Those devices include telescoping tube assemblies that urge the dental arches toward positions of improved alignment. Another telescoping tube assembly for repositioning the dental arches is described in U.S. Pat. No. 5,711,667. U.S. Pat. Nos. 5,562,445 and 5,964,588 also describe intra-oral devices having telescoping members.

In the past, it has been common practice to connect Class II correctors to buccal tubes using a ball pin. Examples of such connections are shown in U.S. Pat. Nos. 6,234,791, 5,964,588 and 5,651,672. As described in those references, a ball pin is threaded through an aperture located adjacent the upper end of the Class II corrector, and then directed through the passage in the buccal tube from its distal side (i.e., the side facing away from the middle of the patient's dental arch) to the mesial side (i.e., the side facing toward the middle of the patient's dental arch). The mesial end of the pin is then bent at an angle to retain the pin in place.

While ball pins provide an inexpensive and secure connection of Class II correctors to buccal tube appliances, there are inherent problems associated with the same. For example, some practitioners encounter difficulty when threading the pin through the buccal tube appliance from its distal side, particularly in instances where space in the oral cavity is restricted. Pliers are often used for placing the pin in the passage of the buccal tube appliance, but if the grip on the pin is lost, the pin may slip out of the aperture of the Class II corrector and become loose in the patient's oral cavity. Furthermore, once the pin has been correctly installed in the passage, it may be difficult to bend the end section of the pin at an angle, especially when a certain orientation is desired.

It has also been proposed in the past to use a retaining clip for connecting Class II correctors to buccal tube appliances. Such clips are somewhat similar to safety pins, in that they have a free end with a straight shank and another end with a hook that can be extended around the shank. Once the free end has been inserted into the passage of the buccal tube appliance, the clip is closed by moving the hook until the hook extends around the shank.

However, the retaining clips described above are not entirely satisfactory because they also are constructed for insertion into the passage of the buccal tube appliance from its distal side to its mesial side. Moreover, it may be difficult and somewhat time-consuming to connect the hook to the shank within the confines of the oral cavity. Clearly, there is a need for a better coupling that overcomes these difficulties.

SUMMARY OF THE INVENTION

The present invention provides an improved coupling for attachment of orthodontic components to each other. The coupling includes a body with a portion that is received in a passage of an orthodontic appliance with a flexible, snap-in retention movement. The snap-in retention obviates the need to place a bend in a coupling in order to secure the coupling to the appliance.

In more detail, the present invention in one aspect is directed toward an orthodontic coupling that comprises a body having a first portion, a second portion and a third portion interconnecting the first portion and the second portion. The second portion is substantially straight and has an outer, free end. The third portion is resilient and enables movement of the outer end toward and away from the first portion. The third portion biases the outer end of the second portion toward a position adjacent the first portion.

Another aspect of the present invention is also directed to an orthodontic coupling. In this aspect, the coupling includes a body having a first portion, a second portion and a third portion interconnecting the first portion and the second portion. The first portion, the second portion and the third portion present an overall, generally "U"-shaped configuration in elevational view and the first portion and the second portion are substantially straight. The first portion and the second portion are resiliently biased in directions toward each other.

Another aspect of the invention is directed toward an orthodontic assembly. The assembly includes a buccal tube having a passage, a force module, and a coupling for connecting the force module to the buccal tube. The coupling includes a body having a first portion and a second portion. The first portion and the second portion are movable toward and away from each other. The second portion is received in the passage and is resiliently biased in a direction toward the first portion in order to releasably retain the body in contact with the buccal tube.

Another aspect of the present invention is also directed toward an orthodontic assembly. In this aspect, the assembly includes a buccal tube having a passage, a Class II corrector and a coupling for connecting the Class II corrector to the buccal tube appliance. The coupling includes a body having a first portion, a second portion and third portion interconnecting the first portion and the second portion. The second portion is received in the passage and has an outer, free end. The third portion is resilient and enables movement of the outer end toward and away from the first portion. The third portion biases the outer end of the second portion toward a position adjacent the first portion in order to releasably retain the second portion in the passage of the buccal tube.

The invention in another aspect is also directed to an orthodontic assembly having a buccal tube with a passage, a force module and a coupling for connecting the force module to the buccal tube. The coupling includes a body having a first portion and a second portion, and the first portion and the second portion are movable toward and away from each other. The second portion has an outer end and is resiliently biased to an orientation such that that outer end is spaced from the first portion. The outer end moves away from the first portion as the second portion is received in the passage.

Preferably, the coupling is constructed such that the portion received in the passage of the buccal tube appliance is inserted in the passage in a distal direction. Such structure enables the practitioner to better view the installation procedure and have better access for manipulation of the coupling. Preferably, the coupling is constructed to position the force module adjacent a distal side of the buccal tube appliance so that the overall working length of the force module is not unduly constrained. Advantageously, the force module in this orientation applies force to the coupling in a distal direction, which further helps to ensure that the coupling does not detach from the buccal tube appliance during the course of treatment.

These and other aspects of the invention are described in more detail in the paragraphs that follow and are illustrated in the accompanying drawings.

DETAILED DESCRIPTION OF THE PREFERRED EMBODIMENTS

Figure 1:
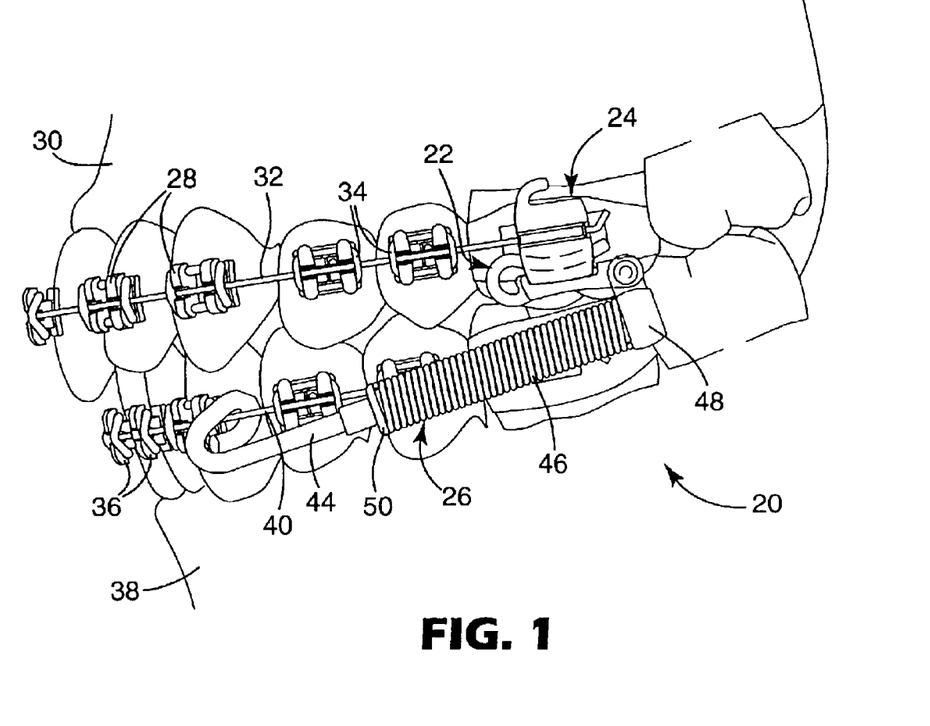
FIG. 1 is a fragmentary side elevational view showing an example of a patient undergoing orthodontic treatment, wherein a coupling of the present invention is used to connect a Class II corrector to a buccal tube appliance mounted on the patient's upper left first molar tooth.

An orthodontic assembly according to one embodiment of the present invention is illustrated in FIG. 1 and is broadly designated by the numeral 20. The assembly 20 includes a coupling 22, a buccal tube appliance 24 and a force module 26. The assembly 20 is connected to other components of a patient undergoing orthodontic treatment.

In FIG. 1, a number of slotted orthodontic brackets 28 are fixed to the teeth of the patient's upper jaw 30 and an archwire 32 is received in the slot of each bracket 28. An elastomeric O-ring ligature 34 extends around tiewings of each bracket 28 in order to urge the archwire 32 toward an orientation seated in the slots.

Similarly, the orthodontic system illustrated in the example shown in FIG. 1 includes a number of lower brackets 36 that are mounted on the teeth of the patient's lower jaw 38. An archwire 40 is received in the slots of the brackets 36 and is held in place by elastomeric O-ring ligatures.

The left distal end of the upper archwire 32 is received in archwire passageway of the buccal tube appliance 24. Optionally, an end section of the archwire 32 is bent as shown in FIG. 1 in a location adjacent the distal side of the buccal tube appliance 24. Preferably, but not necessarily, the archwire passageway of the buccal tube appliance 24 is "convertible" so that it can be opened along its labial side when desired by the practitioner.

The force module 26 is preferably similar to the force module described in U.S. Pat. No. 5,964,588, which is incorporated by reference herein. In brief, the force module 26 includes a first elongated tubular member 43 (see FIG. 3), a second elongated tubular member that is received in the first member in sliding, telescoping relation, and a third member 44 that is received in the second member. A helical compression spring 46 extends around the first tubular member 43 and has an outer end that bears against a connector 48 of the force module 26 that is fixed to the first member 43. The opposite end of the spring 46 bears against an annular fitting 50 that is secured to an outer end section of the second member.

Preferably, the outer end of the third member 44 is formed as shown in FIG. 1 for reception around the lower archwire 40. Also, the outer end of the third member 44 preferably includes a recess for ease of bending the outer end section around the lower archwire 40. The recess is described in pending U.S. patent application Ser. No. 09/687,392, which is incorporated by reference herein.

Preferably, the overall effective length of the force module 26 is selected so that the first and second members are not fully compressed and the second member is not fully inserted into the first member when the patient's jaws are closed. As a consequence, the inherent bias of the spring 46 provides the desired corrective forces by urging the first and second member away from each other in order to thereby move one dental arch relative to the other.

Turning now to the coupling 22, reference is made to FIGS. 2–6 wherein the coupling 22 is shown in more detail. As illustrated, the coupling 22 includes a body 52 having a substantially straight first portion 54, a substantially straight second portion 56 and a third portion 58. The third portion 58 interconnects the first portion 54 and the second portion 56. The second portion 56 has an outer, free end 60 and preferably includes a smooth curve having a relatively large radius of curvature along its entire length. The second portion 56 includes a central apex 62 that is inwardly curved in a direction toward the first portion 54.

Figure 2:
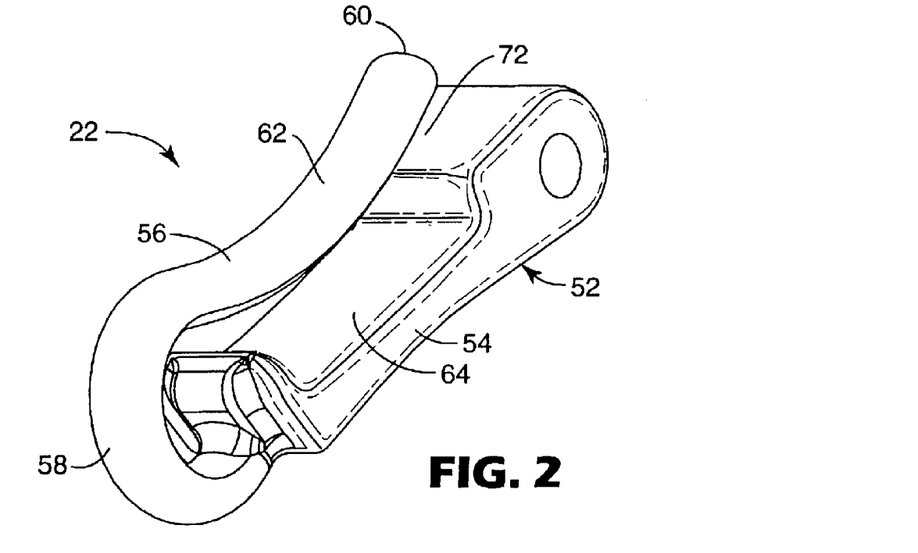
FIG. 2 is an enlarged perspective view of the coupling alone that is shown in FIG. 1, except that a pivot pin for connection to the Class II corrector has been removed.
Figure 3:
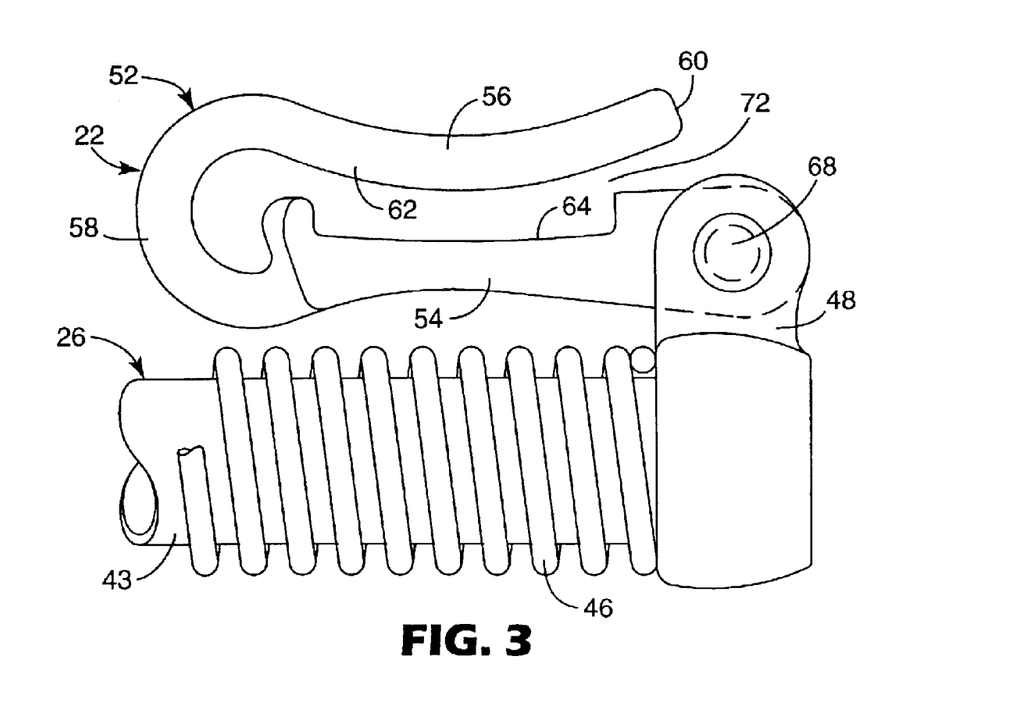
FIG. 3 is an enlarged side elevational view of the coupling shown in FIGS. 1 and 2 along with a portion of the Class II corrector, looking toward the coupling in a lingual direction (i.e., in a direction toward the patient's tongue)
Figure 4:
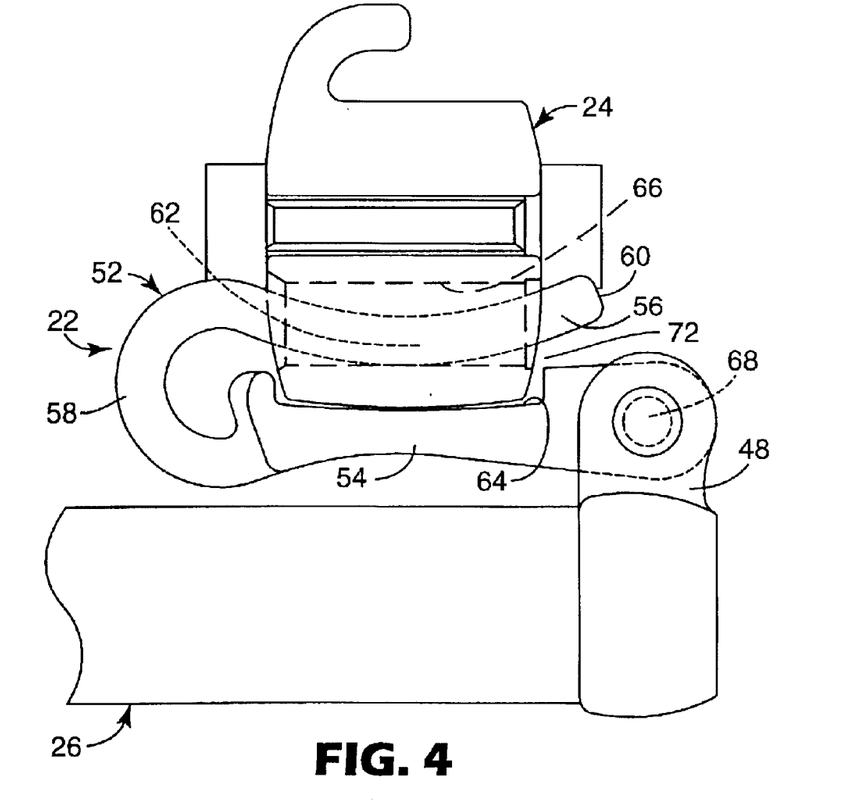
FIG. 4 is a view somewhat similar to FIG. 3 except that the buccal tube appliance is also shown.

The first portion 54 has a somewhat rectangular configuration in plan view along with a recess 64 that extends along its upper, gingival side. As shown in FIGS. 2–4, the curved apex 62 of the second portion 56 extends toward the middle of the recess 64 of the first portion 54. Preferably, the length of the recess 64 in a mesial-distal direction is just slightly greater than the overall, mesial-distal length of the adjacent section of the buccal tube appliance 24 as depicted in FIG. 4 so that buccal tube appliance 24 is received in seated relationship in the recess 64.

The third portion 58 is sufficiently resilient to enable relative movement of the second portion 56 and the first portion 54 in directions toward and away from each other. Preferably, the second portion 56 and the third portion 58 are located as shown in FIGS. 2 and 3 relative to the first portion 54 when the third portion 58 is in its normal, relaxed condition. In this relaxed condition, the second portion 56 including the outer, free end 60 is separated by a space 72 from the first portion 54 and the portions 54, 56 extend in directions that are substantially parallel to each other.

Preferably, but not necessarily, the second portion 56 and the third portion 58 have a transverse cross-sectional configuration that is elliptical or somewhat similar in shape to an ellipse, with the major axis of the ellipse extending in a direction that is parallel to a buccolabial-lingual reference axis. As a result, the portions 56, 58 exhibit increased strength in a lateral direction (i.e., in a buccolabial-lingual direction) to help withstand the forces imposed on the coupling 22 as the patient's jaws 30, 38 move relative to each other. In contrast, the smaller dimension along the minor axis of the elliptical shape enables the portions 56, 58 to exhibit enhanced resiliency in an occlusal-gingival direction so that the first and second portions 54, 56 can be moved away from each other when desired without undue effort.

Figure 5:
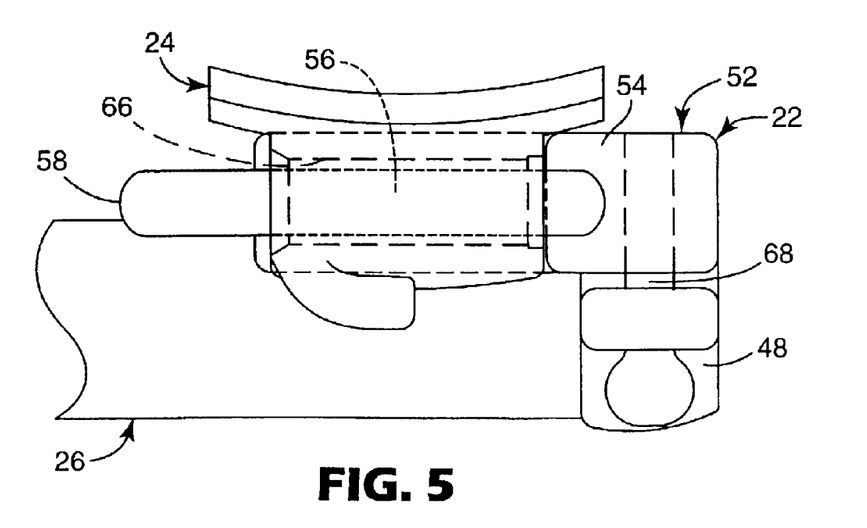
FIG. 5 is an enlarged plan view, looking in an occlusal direction (i.e., in a direction toward the outer tips of the patient's teeth) toward the coupling, the buccal tube appliance and the portion of the Class II corrector illustrated in FIG. 4.
Figure 6:
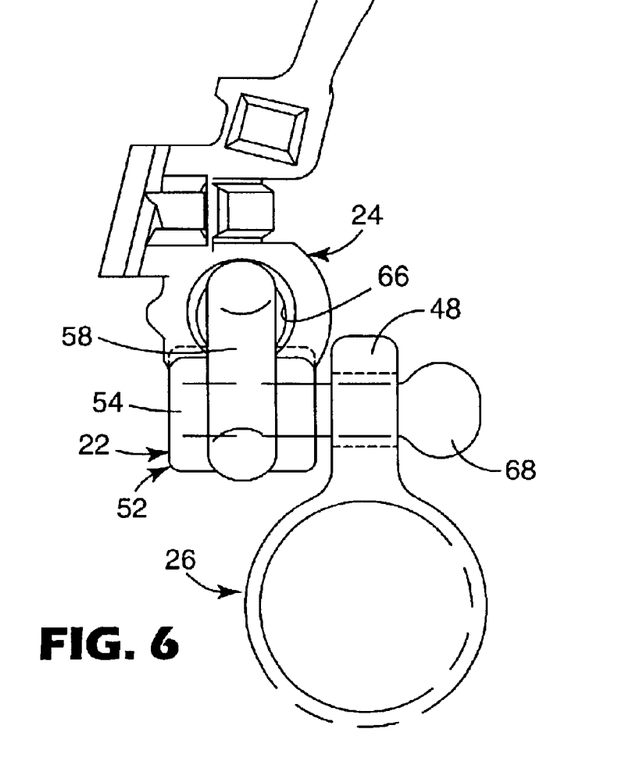
FIG. 6 is an enlarged end elevational view of the coupling, buccal tube appliance and Class II corrector shown in FIGS. 4 and 5, looking in a distal direction.

As shown in FIGS. 4 and 5, the second portion 56 of the coupling 22 is received in an auxiliary passage 66 of the buccal tube appliance 24. During installation, the free end 60 is inserted in the mesial side of the passage 66. As the practitioner continues to press the coupling 22 against the appliance 24 in a distal direction, the portions 54, 56 self-move away from each other a distance sufficient to enlarge the space 72 between the free end 60 and the first portion 54. Such movement is enabled by the inherent resilience of the third portion 58, and optionally may also be facilitated by the inherent resilience of the second portion 56 (which optionally has the same cross-sectional shape as the third portion 58). The curved shape of the second portion 56 near its free end 60 also helps to ease the spreading-apart motion of the portions 54, 56.

As installation of the coupling 24 proceeds, the free end 60 is directed through the passage 66 in a distal direction until such time as it emerges from the distal side of the passage 66. The inherent memory of the third portion 58 (and optionally the second portion 56) relatively moves the portions 54, 56 toward each other and toward the orientation shown in FIG. 4 as the free end 60 moves toward its position illustrated in FIG. 4. At that time, and as depicted in FIG. 4, the adjacent section of the buccal tube appliance 24 is received in the recess 64 of the first portion 54.

The resilience of the body 52, in combination with the shape of the recess 64 enables the appliance 24 to "snap-fit"

into its position in the recess 64. In this position, the wall of the appliance 24 that is located on the occlusal side of the passage 66 is held captive in the recess 64. During treatment, the resilience of the body 52 ensures that this captive relationship continues until such time as the practitioner desires to release the coupling 22 from the appliance 24. In practice, the coupling 22 may be released by pressing on the coupling 22 or the force module 26 in an occlusal direction (i.e. in a downwardly direction viewing the arrangement in FIG. 4) in order to widen the space 72 so that the coupling 22 can then be moved in a mesial direction for disengagement from the appliance 24.

Preferably, the outer free end 60 has an outermost curved or tapered edge for facilitating lateral deflection of the second portion 56 and entry into the passage 66. In addition, the passage 66 preferably has a chamfered mesial entrance as shown by the dashed lines in FIGS. 4 and 5. Such construction eases installation of the coupling 22, especially in locations of the oral cavity where space is limited and viewing of the installation procedure may be difficult.

Preferably, the body 52, including the portions 54, 56, 58, is integral and fabricated as a single component. Optionally, the body 52 may be made by a metal injection molding process using a heat treatable material such as 17-4 PH stainless steel. As another alternative, the body 52 may be made by a milling process.

The coupling 22 is pivotally connected to the connector 48 of the force module 26 by a pin 68 (see, e.g., FIGS. 3–6). The pin 68 extends through an aperture of the connector 48 and has an outer, enlarged head to prevent disengagement from the connector 48. The pin 68 may be secured to the body 52 by any suitable means such as tack welding, an interference fit or the like.

Advantageously, the shape of the first portion 54 substantially prevents excessive rotation of the coupling 22 in directions along an arc about an axis parallel to the central axis of the passage 66. The generally flat lingual wall of the first portion 54, in combination with the shape of the outer surface of the adjacent band (i.e., the molar band upon which the appliance 24 is mounted) or alternatively, the outer surface of the patient's tooth (i.e., the molar tooth upon which the appliance 24 is mounted), helps to prevent such rotation. As a consequence, rotation of the force module 26 is also limited.

Additionally, the exemplary coupling 22 as shown in the drawings is located in an orientation where it is unlikely to cause undue interference with other orthodontic components in the patient's oral cavity or with the patient's soft tissue, such as the adjacent soft tissue of the cheeks. Such construction helps ensure that the coupling 22 as well as the other components will not be damaged during the course of treatment and that the likelihood of injury to the patient's soft tissue is reduced. As an additional advantage, the body 52, when symmetrically constructed as shown in the drawings, can be assembled for use on either the right side or the left side of the patient's dental arches so that the number of different parts that must be manufactured is also reduced.

An orthodontic coupling 22a according to another embodiment of the invention is illustrated in FIGS. 7-10. The coupling 22a includes a body 52a that in this instance is made from a single formed section of wire stock. The body 52a includes a substantially straight first portion 54a, a substantially straight second portion 56a and a third portion 58a that interconnects the first portion 54a and the second portion 56a. In this illustration, the coupling 22a is adapted for installation on the upper right hand side of the patient's oral cavity.

The portions 54a, 56a, 58a present an overall, generally "U"-shaped configuration in their normal, relaxed configuration with the portions 56a, 58a extending generally parallel to each other. The third portion 58a is resilient and enables the first portion 54a and the second portion 56a to relatively move toward and away from each other. The portions 54a, 56a, 58a are shown in their relaxed configurations in the drawings.

Figure 7:
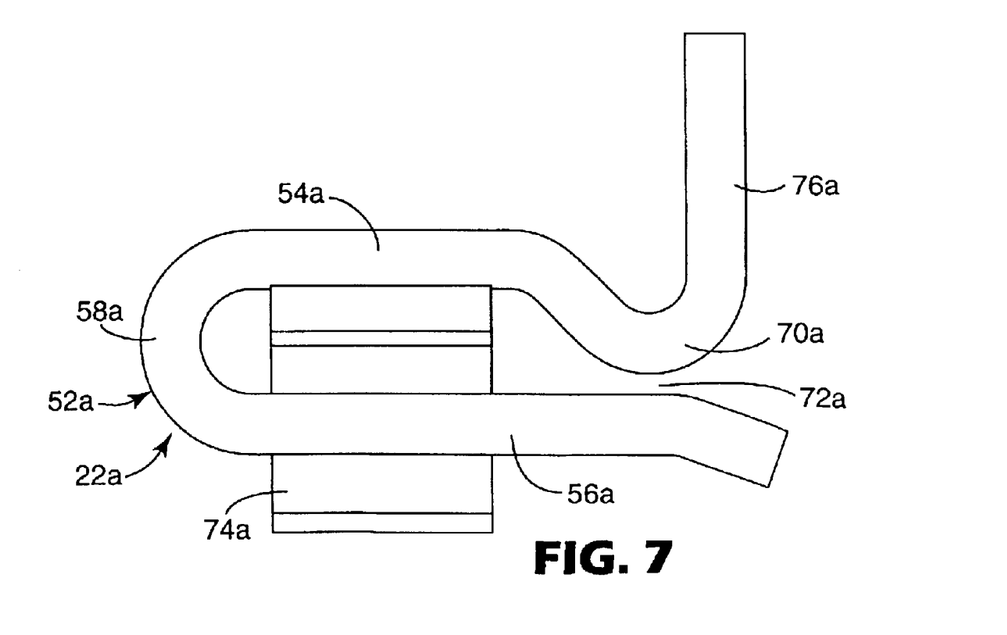
FIG. 7 is an enlarged side elevational view of an orthodontic coupling constructed according to another embodiment of the invention, looking downwardly in an occlusal direction.

The body 52a includes a recurve segment 70a that extends toward the second portion 56a. When the portions 54a, 56a, 58a are in normal relaxed configuration, the recurve segment 70a is closely adjacent the second portion 56a, separated by a space 72a. Preferably, an outer, free end of the second portion 56a is bent at a slight angle as shown in FIGS. 7 and 9 in order to facilitate entry of the second portion 56a into the passage of a buccal tube appliance.

Figures 8, 10:
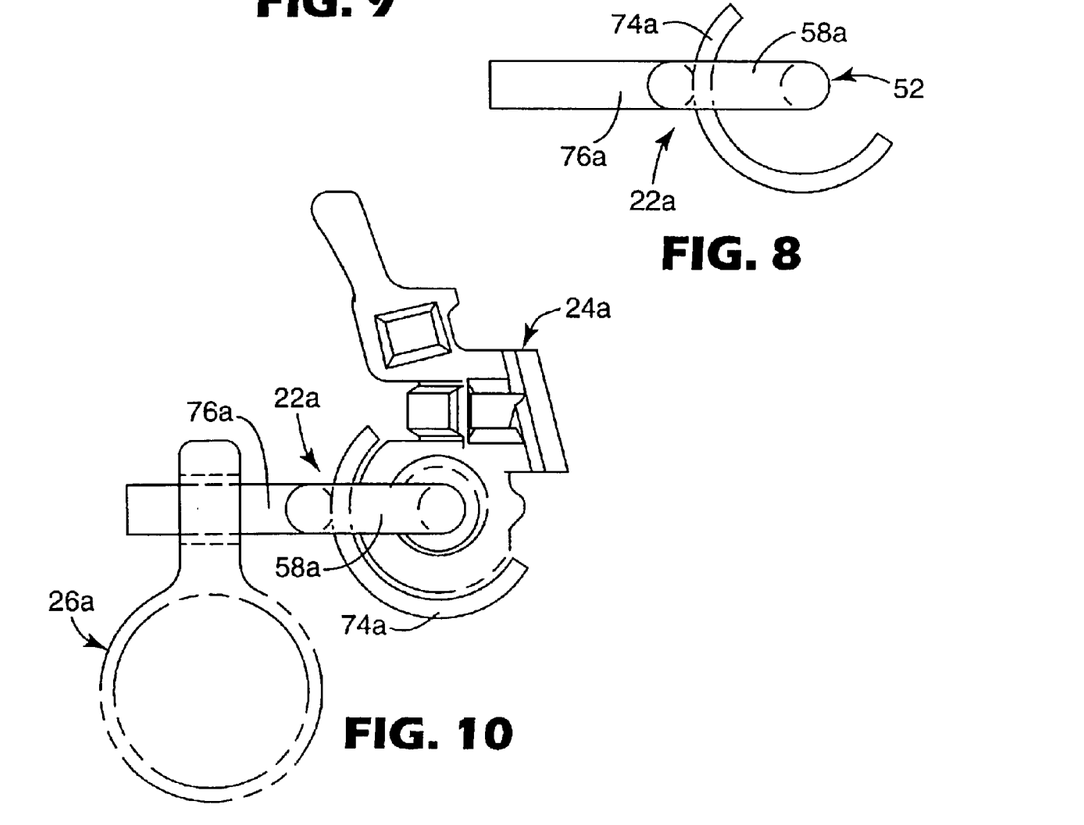
FIG. 8 is an enlarged end view of the coupling shown in FIG. 7, looking in a distal direction.
FIG. 10 is a view similar to FIG. 8 except that the buccal tube appliance and the Class II corrector shown in FIG. 9 have been added.
Figure 9:
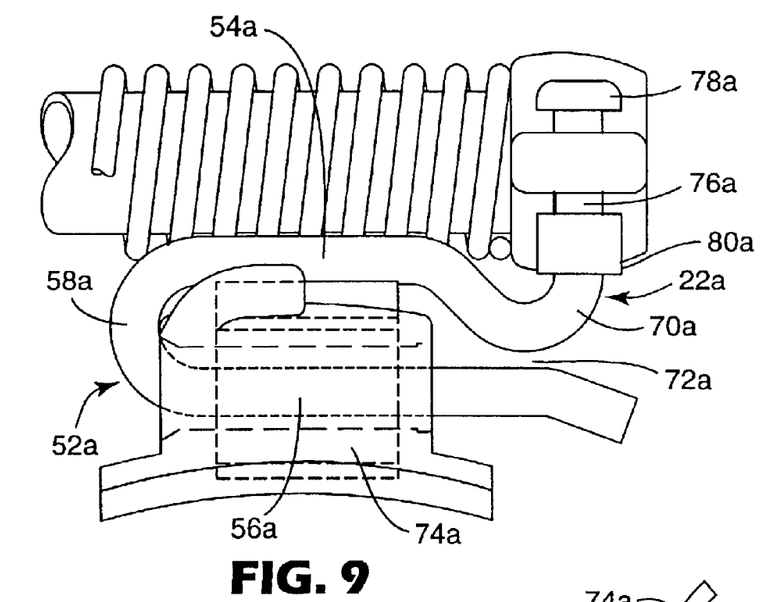
FIG. 9 is a view similar to FIG. 7 but additionally showing an exemplary buccal tube appliance and Class II corrector.

During insertion the second portion 56a into the passage of a buccal tube appliance, such as the passage 66a of the appliance 24a shown in FIGS. 9 and 10, the portions 54a, 56a deflect and spread apart due to the inherent resiliency of the third portion 58a. The portions 54a, 56a shift apart a distance sufficient to enable the buccal tube appliance to pass through the now enlarged space 72a as the coupling 22a continues to move in a distal direction. During such movement, the space 72a enlarges as needed to accommodate the thickness of the wall of the appliance 24a that is located on the buccolabial side of the passage 66a.

Once the buccal tube appliance 24a is received in the position shown in FIGS. 9 and 10 and is located on the mesial side of the recurve segment 70a, the portions 54a, 56a self-return to their positions adjacent each other due to the inherent bias presented by the third portion 58a. Thereafter, the reduced space 72a serves to retain the coupling 22a in place on the buccal tube appliance 24a.

Preferably, the coupling 22a includes a stop 74a to limit relative rotation of the coupling 22a and the buccal tube 24a in a direction along an arc about the major longitudinal axis of the second portion 56a. In the embodiment shown in the drawings, the stop 74a is constructed by fixing a curved wall to the first portion 54a. Optionally, the curved wall is cut from a section of stainless steel tubing and is welded or brazed to the first portion 54a.

The body 52a also includes a pivot portion 76a that functions in the manner similar to the pivot pin 68 described above. The pivot portion 76a is received in an aperture of a connector 48a of a force module 26a. The pivot portion 76a extends in a direction generally perpendicular to the major direction of extension of the second portion 56a.

An outer end of the pivot portion 76a is provided with a retainer 78a in order to prevent disconnection of the coupling 22a from the force module 26a. The coupling 22a is also provided with a spacer 80a on the opposite side of the connector 48a. The spacer 80a functions as a stop to prevent the connector 48a from entering the bend of the body 52a that extends along the recurve segment 70a.

The embodiments described above and shown in the accompanying illustrations are illustrative of the present invention and should not be deemed limiting. Those skilled in the art may recognize that other couplings may be constructed that utilize the principles of the present invention. Moreover, the couplings described above may be used in conjunction with other types of force modules, such as the numerous other Class II correction devices described in the patents set out above. Accordingly, the invention should not be limited to the details set out above, but instead only by a fair scope of the claims that follow along with their equivalents.

What is claimed is:

1. A method of assembling an orthodontic assembly comprising:
providing a buccal tube having a passage with a mesial side;
connecting a coupling to a force module, wherein the coupling includes a body with a first portion and a second portion and wherein the second portion includes a free end;
inserting the free end of the second portion into the mesial side of the passage; and
pressing the coupling against the buccal tube in a distal direction in order to self-move the first portion and the second portion away from each other and provide sufficient space to receive the second portion in the passage, wherein the coupling has sufficient memory to relatively self-move the first portion and the second portion toward each other once the second portion is received in the passage, and wherein the second portion is resiliently biased in a direction toward the first portion with sufficient force to releasably retain the body in contact with the buccal tube.

2. The method of claim 1 wherein the first and second portions comprise an integral section of wire.

3. The method of claim 1 wherein the coupling is made by a metal injection molding process.

4. The method of claim 1 wherein the first portion includes a recess, and wherein the second portion includes a curve that extends toward the recess when the second portion is received in the passage.

5. The method of claim 1 wherein the second portion includes a section that is substantially straight, and wherein the first portion includes a section that generally extends in a direction substantially parallel to the straight section of the second portion.

6. The method of claim 5 wherein the first portion includes a recurve segment that is adjacent the free end of the second portion.

7. The method of claim 1 wherein the second portion has a major longitudinal axis and wherein the coupling includes a stop to limit relative movement of the coupling in directions along an arc about the longitudinal axis.

8. The method of claim 1 wherein the passage has a central axis, and wherein the coupling is pivotally connected to the force module for movement in an arc about an axis that is generally perpendicular to the central axis when the second portion is received in the passage.

9. The method of claim 1 wherein the buccal tube has a distal side and wherein the second portion has a free end that is adjacent the distal side when the second portion is received in the passage.

10. The method of claim 1 wherein the second portion has a cross-sectional configuration that resembles an ellipse.

11. An orthodontic assembly comprising:
a buccal tube having a passage;
a Class II corrector, and
a coupling for connecting the Class II corrector to the buccal tube, the coupling including a body having a first portion, a second portion adjacent the first portion and a third portion interconnecting the first portion and the second portion, wherein the second portion is received in the passage and has an outer, free end, wherein the third portion is resilient and enables self-movement of the outer end away from the first portion as the coupling is pressed against the buccal tube, wherein the second portion is inserted in the passage, wherein the coupling has sufficient memory to relatively self-move the outer end toward the first portion once the second portion is received in the passage, and wherein the third portion biases the outer end of the second portion toward a position adjacent the first portion with sufficient force to releasably retain the second portion in the passage of the buccal tube.

12. An orthodontic assembly according to claim 11 wherein the first, second and third portions comprise an integral section of wire.

13. An orthodontic assembly according to claim 11 wherein the coupling is made by a metal injection molding process.

14. An orthodontic assembly according to claim 11 wherein the first portion includes a recess, and wherein the second portion includes a curve that extends toward the recess.

15. An orthodontic assembly according to claim 11 wherein the second portion includes a section that is substantially straight, and wherein the first portion includes a section that generally extends in a direction substantially parallel to the straight section of the second portion.

16. An orthodontic assembly according to claim 15 wherein the first portion includes a recurve segment that is adjacent the outer end of the second portion.

17. An orthodontic assembly according to claim 11 wherein the second portion has a major longitudinal axis and wherein the coupling includes a stop to limit relative movement of the coupling in directions along an arc about the longitudinal axis.

18. An orthodontic assembly according to claim 11 wherein the passage has a central axis, and wherein the coupling is pivotally connected to the force module for movement in an arc about an axis that is generally perpendicular to the central axis.

19. An orthodontic assembly according to claim 11 wherein the buccal tube has a distal side and wherein the second portion has a free end that is adjacent the distal side.

20. An orthodontic assembly comprising:
a buccal tube having a mesial side, a distal side and a passage;
a Class II corrector, and
a coupling for connecting the Class II corrector to the buccal tube, the coupling including a first portion connected to the Class II corrector and a second portion with a free end, wherein the free end is inserted into the passage in a direction from the mesial side to the distal side in order to locate the free end adjacent the distal side, wherein the connection between the first portion and the Class II corrector is located adjacent the distal side, and wherein the first portion includes a recurve segment that is adjacent the outer end of the second portion.

21. An orthodontic assembly according to claim 20 wherein the connection between the first portion and the Class II corrector comprises a pin.

22. An orthodontic assembly according to claim 20 wherein the first and second portions comprise an integral section of wire.

23. An orthodontic assembly according to claim 20 wherein the second portion has a major longitudinal axis and wherein the coupling includes a stop to limit relative movement of the coupling in directions along an arc about the longitudinal axis.

24. An orthodontic assembly comprising:

a buccal tube having a mesial side, a distal side and a passage;

a Class II corrector; and a coupling for connecting the Class II corrector to the buccal tube, the coupling including a first portion connected to the Class II corrector and a second portion with a free end, wherein the free end is inserted into the passage in a direction from the mesial side to the distal side in order to locate the free and adjacent the distal side, wherein the connection between the first portion and the Class II corrector is located adjacent the distal side, wherein the first portion includes a recess, and wherein the second portion includes a curve that extends toward the recess.

25. An orthodontic assembly comprising:

a buccal tube having a passage;

a Class II corrector; and a coupling for connecting the Class II corrector to the buccal tube, the coupling including a body having a first portion, a second portion and a third portion interconnecting the first portion and the second portion, wherein the second portion is received in the passage and has an outer, free end, wherein the third portion is resilient and enables movement of the outer end toward and away from the first portion, wherein the third portion biases the outer end of the second portion toward a position adjacent the first portion in order to releasably retain the second portion in the passage of the buccal tube, and wherein the second portion includes a curve that extends toward the recess.

26. An orthodontic assembly comprising:

a buccal tube having a passage;

a Class II corrector; and a coupling for connecting the Class II corrector to the buccal tube, the coupling including a body having a first portion, a second portion and a third portion interconnecting the first portion and the second portion, wherein the second portion is received in the passage and has an outer, free end, wherein the third portion is resilient and enables movement of the outer end toward and away from the first portion, and wherein the third portion biases the outer end of the second portion toward a position adjacent the first portion in order to releasably retain the second portion in the passage of the buccal tube, wherein the second portion includes a section that is substantially straight, wherein the first portion includes a section that generally extends in a direction substantially parallel to the straight section of the second portion, and wherein the first portion includes a recurve segment that is adjacent the outer end of the second portion.

* * * * *